(12) United States Patent
Mokshagundam et al.

(10) Patent No.: US 6,599,522 B2
(45) Date of Patent: Jul. 29, 2003

(54) TRIGLYCERIDE REDUCING AGENT

(76) Inventors: Lakshminarayan Rao V. Mokshagundam, deceased, late of Bangalore Kar (IN); by Mokshagundam L. Sharada, legal representative, 462, 17 'G' Main, Koramangala VI Block, Bangalore Kar (IN)

(*) Notice: Subject to any disclaimer, the term of this patent is extended or adjusted under 35 U.S.C. 154(b) by 20 days.

(21) Appl. No.: 09/995,713

(22) Filed: Nov. 29, 2001

(65) Prior Publication Data
US 2002/0102299 A1 Aug. 1, 2002

Related U.S. Application Data
(60) Provisional application No. 60/250,143, filed on Dec. 1, 2000.

(51) Int. Cl.[7] .......................... A61K 47/00; A61K 9/14; A61K 9/20; A61K 9/48; A61K 9/64

(52) U.S. Cl. .................. 424/439; 424/400; 424/451; 424/456; 424/464; 424/465; 424/489

(58) Field of Search ................................. 424/400, 439, 424/451, 456, 464, 465, 489

(56) References Cited

U.S. PATENT DOCUMENTS

| | | | |
|---|---|---|---|
| 4,287,368 A | | 9/1981 | Johson et al. |
| 5,034,215 A | | 7/1991 | Santa-Coloma Roth |
| 5,674,498 A | | 10/1997 | Inoue et al. |
| 5,840,991 A | * | 11/1998 | Yeng et al. |
| 5,895,657 A | * | 4/1999 | Fournet et al. |
| 6,248,363 B1 | * | 6/2001 | Patel et al. |

OTHER PUBLICATIONS

Srinivasan, M.R.; Chandrasekhara, N.; "Comparative influence of vanillin & capsaicin on liver & blood lipids in the rat", Indian J Med Res, 96 (Apr. 1998), pp 133–135.*

DJ Abraham et al., "Vanillin, a potential agent for the treatment of sickle cell anemia," Blood, vol. 77, issue 6, Mar. 15, 1991, pp. 1334–1341. (Summary).

* cited by examiner

Primary Examiner—Thurman K. Page
Assistant Examiner—Simon J. Oh
(74) Attorney, Agent, or Firm—Litman Law Offices, Ltd.

(57) ABSTRACT

The use of vanillin as a hypolipidemic—a hypotriglyceridemic pharmaceutical agent over a wide range of concentration in the treatment of diabetes (type-2), cardiovascular disturbances, and obesity. Vanillin is also used as a food additive for preventing the development of such pathological conditions, particularly in young people.

12 Claims, 3 Drawing Sheets

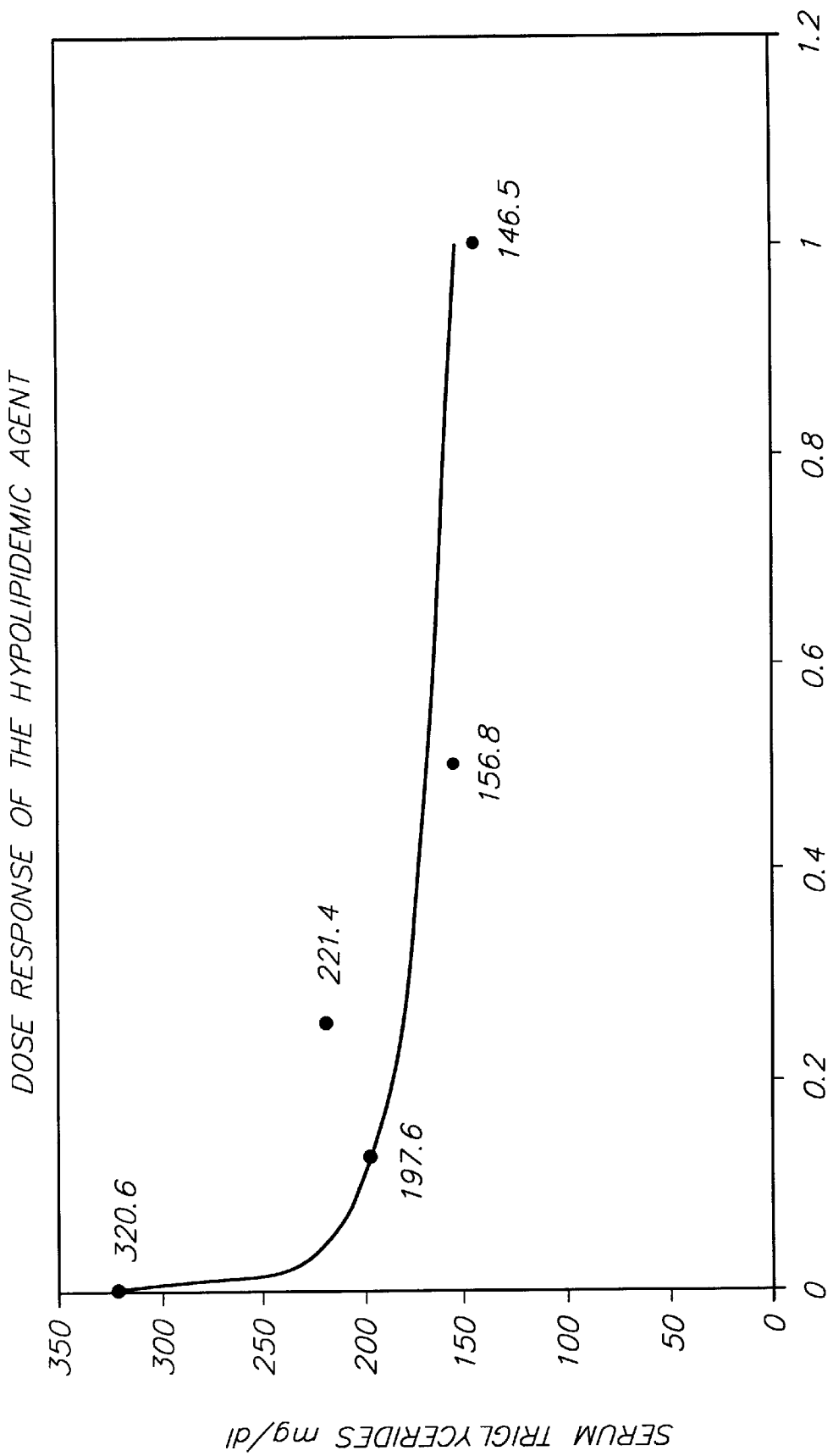

TRIGLYCERIDE REDUCING AGENT

CROSS-REFERENCE TO RELATED APPLICATION

This application claims the benefit of U.S. Provisional Patent Application Serial No. 60/250,143, filed Dec. 1, 2000.

BACKGROUND OF THE INVENTION

1. Field of the Invention

The present invention relates to triglyceride reducing agents for use in the human body, and, more particularly, a flavour compound for prevention and treatment of hyperlipidemia (hypertriglyceridemia).

2. Description of Related Art

The consumption of foods with high content of fat and sugar is on the rise. This leads to an increasing number of cases suffering from hyperlipidemia, a major pathologic metabolic change accompanying several disorders such as obesity, diabetes, and cardiac disturbances. Particularly, it affects children of the growing age. A dietary formulation or dietary supplement or a specific hypolipidemic agent which is easy to use, with no side effects and absolutely non-toxic over a wide range would be the ideal goal.

Recent scientific reports indicate that in some of the pungent spices the main active components possess the desirable hypolipidemic and/or hypocholesterolimic activities. Many of these spices find wide use as medicinal components in the native countries. India is foremost among the countries which consume spices, particularly of the hot, pungent type. Some, such as pepper, ginger, and turmeric are native to the country. Chillies or capsicums have been imported from Mexico, but adopted into its dietaries and has become native to India.

Extensive nutritional studies have indicated that the pungent spices as well as the milder turmeric and their principal active constituents have no adverse toxic effects as judged by the effects on growth, internal organs, nitrogen balance and blood chemistry. Some of these spices seem to have special nutritional virtues like beneficial effects of reducing the cholesterol and lipid levels in the blood and some of the special internal organs such as the liver, the kidney, and the heart. They are now slowly getting adopted into special therapeutic preparations or nutritional formulae for the treatment of diseases which seem to originate from specific disturbances in lipid metabolisms, such as diabetes, cardiovascular diseases and obesity. Adequate intakes of some of these spices in normal human dietaries may also provide good protection against these types of diseases.

The main pharmacological property of turmeric, which it owes to curcumin, is hypocholesterolemia, which involves the stimulation and formation of bile. Curcumin, through this function of excreting bile, helps prevent the formation of bilestones. More recently, the anti-carcinogenic activity of curcumin has been demonstrated in several experimental and clinical studies. For this purpose, a specially concentrated combination of the three active curcumins has been developed. Clinical studies are in progress at several research centers. There has also been a revival of interest in the antioxidant and anti-inflammatory properties of the active component of turmeric.

Extensive nutritional studies on capsaicin have exhibited the hypolipidemic property of the spice component, alone, or with other spice combination, on the lipid metabolism at different dietary levels of the spice. These studies serve to firmly establish it's fat mobilizing (lipotropic) action on the liver and also stimulation of fat utilization in peripheral tissues through activation of lipoprotein lipase. Also, in some of the studies on liver lipid mobilization, simultaneous mobilization of cholesterol was noticed somewhat similar to the reported activity of turmeric, curcumin, and ginger.

Nutritional evaluation of whole chilli and extracts (capsaicinoids) at low to maximum use levels and even five to ten times the maximum did not adversely affect the growth, nitrogen metabolism, lipid or amino acid absorption. On the contrary, some beneficial effects on lipid metabolism with high fat or high carbohydrate food intake were shown at the higher levels. Hypocholesterolimic effect with a high fat diet, significant in lowering of liver and serum triglycerides and serum lipoprotein triglycerides, has been observed.

Toxicological tests with chillies, chilli extracts and capsaicin and dihydrocapsaicin have established that they are non-mutagenic and non-carcinogenic. Examination of the tissues of the experimental animals fed fairly high levels of the spices have also demonstrated that they are non-carcinogenic.

One of the main physiological responses to capsaicin, even at extremely low doses, is pain production through interaction with nociceptive neurons which give rise to heat production. This involves specifically the capsaicin receptor recently identified as a heat activated ion channel in the pain pathway. Capsaicin and similar molecules have been employed for the relief of pain through heat generation. The thermogenic reaction of capsaicin requires the acid-amide group to be incorporated into the basic vanillin structure which does not have any such heat generating property.

In the first paper published by the inventor on red pepper and capsaicin in 1978, it is suggested that the hypocholesterolimic and hypolipidemic activity which is exhibited by turmeric and curcumin, and also ginger (gingerol), known as the vanilloid spices, implicate the vanillyl moiety as the most probable active component which all these structures seem to share. In other investigations on dihydro-capsaicin, vanillin and vanillin derivative were detected in the urine of the experimental rats, which led to the first experiment on the influence of vanillin on the liver and blood lipids in rats. This comparative study(0.15 mg % vanillin and 0.3 mg % capsaicin) showed a 24% and 13% reduction in serum triglycerides, respectively. These experimental findings, along with all the other experimental data reported on capsaicin and its metabolic effect, stimulated interest in pursuing the hypolipidemic studies on vanillin with planned clinical investigations for determining its therapeutic efficacy as a hypolipidemic agent in diabetes, obesity, and atherosclerotic conditions.

U.S. Pat. No. 5,674,498, issued Oct. 7, 1997, to Inoue et al. describes a blood lipid depressant with an extract from the senna species and vanilla (see Example 11 in column 7).

U.S. Pat. No. 5,034,215, issued on Jul. 23, 1991, to Santa-Coloma Roth describes a nail conditioning composition with vanilla extract.

U.S. Pat. No. 4,287,368, issued on Sep. 1, 1981, to Johnson et al. describes a method for preparing vanillin.

Chinese Patent document 1167581, published Dec. 17, 1997, to Zhang describes a beverage composition comprising sugar, maltose, corn flour, rice flour, starch, table salt, de-fatted milk powder, vanillin, biologic calcium carbonate, high-quality oats flour, and highland barley flour. The Ahang beverage serves to make bones stronger, decrease blood fat and cholesterol, and nourishes the blood.

None of the above inventions and patents, taken either singly or in combination, is seen to describe the instant invention as claimed.

SUMMARY OF THE INVENTION

The present invention provides for vanillin, extracted naturally from vanilla pods, or derived from synthetic derivatives, mixed with other food additives and nutritional and processing agents as a fat reducing agent. This material is then processed into readily usable additive agents or used in the production of food. The vanillin helps reduce the blood fat levels in adults or children. The use of the vanillin additives in fat or sugar rich, foods promotes the utilization of lipids and prevents their diversion into irregular metabolic routes, resulting in pathological toxins, such as cholesterol.

Accordingly, it is a principal object of the invention to provide food additives to affect the reversal of hyperglyceridemia in humans to normal with consequent relief of pathologic clinical symptoms.

It is another object of the invention to provide a combination of effective treatment procedures as above for adoption as needed.

It is a further object of the invention to use the above-mentioned additives and treatment procedures for growing children, and adults having a tendency to adiposity, by adding adequate quantities to milk and manufactured milk products.

Still another object of the invention is to provide chocolates (milk and other types) having the above-mentioned additives to promote efficient physiological utilization of the lipids O (fats) in these foods, especially when excess amounts are likely to be ingested occasionally or habitually.

Yet another object of the invention is to provide for addition of additives to processed sweets and excessively fatty or sugary foods having the objective of preventing obesity in humans.

These and other objects of the present invention will become readily apparent upon further review of the following specification.

BRIEF DESCRIPTION OF THE DRAWINGS

FIG. 3 is a chart illustrating reduction of serum triglycerides in rats for various test formulations of the pharmaceutical of FIG. 1.

DETAILED DESCRIPTION OF THE PREFERRED EMBODIMENTS

Figure 1:
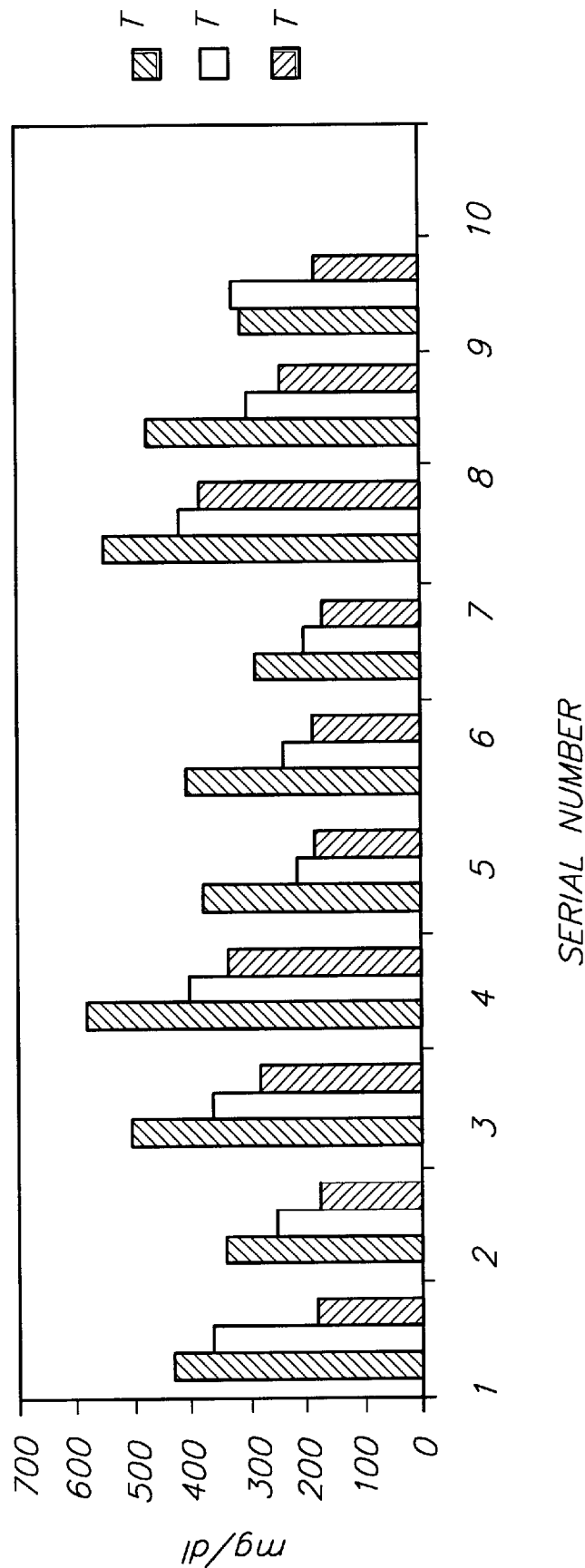
FIG. 1 is a chart illustrating reduction of serum triglycerides in 10 patients by the pharmaceutical of the present invention.

The present invention provides for vanillin, extracted naturally from vanilla pods, or derived from synthetic derivatives, mixed with other food additives and nutritional and processing agents as a fat reducing agent. This material is then processed into readily usable additive agents or used in the production of food. The vanillin helps reduce the blood fat levels in adults or children. The use of the vanillin additives in fat or sugar rich foods promotes the utilization of lipids and prevents their diversion into irregular metabolic routes, resulting in pathological toxins, such as cholesterol.

Vanillin is a choice flavour agent extensively used in baked goods, ice creams, and desserts, and very many types of beverages. It is almost non-toxic and can be freely used in milk and other nutritional beverages, given to children. Vanillin has been given GRAS (generally regarded as safe) status by the Flavour And Extract Manufacturers Association (FEMA) and recognized for use by the Food and Drug Administration (FDA).

"Vanillin, 4-hydroxy-3-methoxybenzaldehyde, is a flavorant present in foods, beverages, and tobacco. The highest average level of use reported in the United States is 768 ppm in confectioneries and frostings. The estimated daily intake is 11 mg/capita and possible average daily intake of vanillin from foods is 38.9 mg/capita. Acute oral $LD_{50}$s are as follows: rat, 1.58 g/kg, guinea pigs, 1.40 g/kg; and rabbits, 3.0 g/kg. Several oral toxicity studies with rats were reported in which high levels of vanillin were consumed for extensive periods without adverse effects. For example, vanillin at 1.0% of the diet for 16 weeks, 0.1% for 27 to 28 weeks, 2.0% and 5.0% for one year, and 0.5%, 1.0% and 2.0% for two years resulted in no significant differences between test and control rats with respect to body and organ weights, hematology, and histopathology. The highest level consumed without adverse effect(5%) in rats is approximately equal to a daily intake of 2500 mg/kg and is nearly 14,000 times the estimated per capita daily intake for a 60-kg person. A much earlier study reported growth depression and organ enlargement with rats on a 5% diet of vanillin for 90 days; however, no adverse effects were observed when rats were administered vanillin orally, either twice per week (300 mg/kg/dose) for 14 weeks, or once a day (20 mg/kg/d) for 126 days. In man, vanillin is converted to vanillic acid in the liver and is excreted in the urine. Vanillic acid is also produced in the body as a result of the breakdown of epinephrin to norepinephrine "(*Blood*, 77,1334–1341, 1991).

In view of the almost non-toxicity of vanillin recognized by the FDA under human food use conditions, it was decided to test chosen formulations of clinical tests on proper cases of diabetes (with stabilized blood sugar levels under treatment with oral hypoglycemic agents), atherogenic cardiovascular cases and a few cases of obesity.

The invention is a combination of the following components in proportion indicated as follows: vanillin 20–2000 mg, ascorbic acid 10–15 mg and ethylenediaminetetraacetic acid (EDTA) 5–10 mg. The mix is ground to 100–120 mesh size and filled into gelatin capsules. The EDTA is an anti-oxidative protectant to preserve the ascorbic acid in the reduced state. The reduced ascorbic acid protects the aldehydic group of vanillin also in the natural reduced condition in the environmental temperature ranges. It is also effective in protecting the ascorbic acid added to baked goods, beverages, and other food preparations when they are put through the normal processing procedures.

TEST EXAMPLE 1

Effect (in vivo) of the Hypolipidemic Agent on Elevated Triglyceride Levels in Blood-Clinical Study Patients attending the Endocrinology and Metabolism outpatient department of M. S. Ramiah Medical College Hospital were included in the study. Patients with baseline serum total cholesterol above 200 mg/dl and/or serum triglycerides above 200 mg/dl after 6–12 weeks of low fat diet, exercise and weight reduction program, were included in the study. The compliance of the subjects for diet, weight and exercise schedules were monitored throughout the study.

The number of patients recruited for the study were 37, including a boy aged five years. There were seven women and 29 men in the age group of 30 to 62 years. Of the 37 patients, 23 patients were diabetic (type two diabetes) and 16 patients had essential hypertension, and two women and nine men were obese, the others being of normal weight. Two men and one woman dropped out of the study, due to unknown causes. Of the original patients, 34 completed the study as per the protocol.

In the initial visit, patient's height in centimeters, and weight in kilograms were recorded. After noting detailed history, physical examinations were performed on each patient. Informed consent was taken from all patients and, in the case of minors, from their parents. Blood samples were drawn for routine hematology, fasting and post prandial plasma glucose, blood urea, serum creatinine, liver function test and lipid profile. At each visit, the patient's weight and diet and exercise compliance was checked and blood samples for hematology and lipid profile were drawn. The patients were given 20 mg of Vanillin in gelatin capsule once a day before the main meal. At each visit, pill count was done to check the compliance of the drug intake. The data were recorded in the case record form and computer by authorized persons. The data were analyzed statistically.

Results

Figure 2:
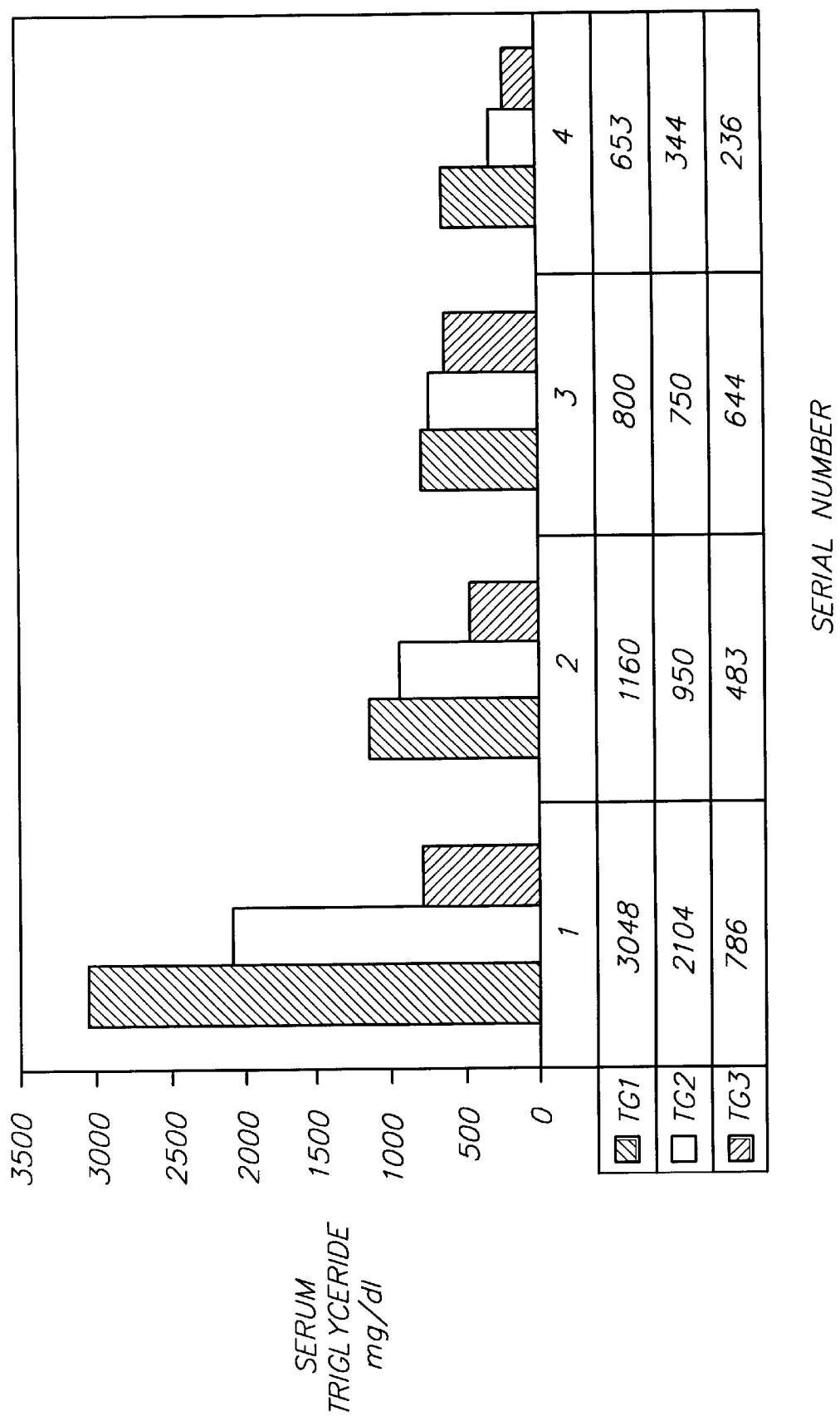
FIG. 2 is a chart and table illustrating responses in four patients under conditions similar to that of FIG. 1, where the initial triglyceride levels were very much higher.

The serum triglycerides reduced significantly in 10 patients (See table 1, below, and FIG. 1) from a mean of 425.2 mg/dl to 230.3 mg/dl ($P<0.0005$) corresponding to a mean value of 46.34% as shown in Table 1. The responses in four other cases where the initial triglyceride levels were very much higher are shown in Table 2 (included in FIG. 2). Even here, the reductions are significant and, in the case of the five-year-old youngster, extraordinarily so (up to 75% reduction) from an initial value of 3078 mg/dl to 786 mg/dl in about six weeks.

There was no difference between the diabetic and non-diabetic group in terms of response. Both of the groups responded well. The serum cholesterol reduced significantly in 20 patients; in others there was no response. The change from baseline total cholesterol was from 16 to 185 mg/dl (mean of 74.5 mg/dl). There was no significant change in the serum HDL level. No adverse effects were noticed in any of the patients. The routine biochemistry, hematology and liver function tests did not show any significant change throughout the study.

The results showed that doses of 20 mg/day oral Vanillin significantly reduced serum triglycerides and total cholesterol in hyperlipidemic patients. The lipid levels did not come to normal as the dose used was probably insufficient.

The study was conducted at the Dept. of Endocrinology, M. S. Ramiah Medical College Hospital, M. S. R. Nagar Bangalore-54.

TEST EXAMPLE 2
Dose Response Spectrum of the Hypolipidemic Agent—Animal Assay:

The response in terms of the lowering of triglyceride component in the majority of the human cases were encouraging. This initiated a dose response test in young adult rats to determine a standard response curve. Such a curve would help in choosing the proper doses for further clinical trials and determine the adequacy and nature of the response.

The tests were done on groups of young Wistar male rats, statistically distributed on the basis of body weight (125±5 g) into six groups, including a control group. The control group received 0% vanillin and the five experimental groups 0.125%, 0.25%, 0.5%, 1.0% and 5% vanillin in the diet. The basal hyperlipidemic diet contained (g/100): casein 15, corn starch 40, cane sugar 10, hydrogenated fat 25, refined peanut oil 5, NRC vitamin mixture (choline free) 1, and salt mixture (Bernhardt-Tomarrelli modified) 4. Fat soluble vitamins at desired concentrations were added to the peanut oil. Vanillin was incorporated into the hyperlipidemic diet in replacement of starch at the desired levels. The duration of the test feeding period was six weeks. At the end of the experimental period, the rats were sacrificed and lipid analysis was done using standard procedures.

Results

Liver weights were not affected at any of the levels tested. Adipose fat was lowered at 1% and 5% levels of test formulation.

Significant hypotriglyceridemic effect was brought about by the test formulation at all levels examined(31–% 54% lowering of serum triglyceride). This lowering was evident in both HDDL and LDL-VLDL fractions.

Significant hypocholesterolemic effect was also noticed (18% and 12% lowering, respectively) in diet groups of 0.125 and 0.25% of test formulation. This lowering effect was mainly confined to LDL-VLDL fraction. Additionally, there was a 16% decrease in HDL cholesterol of the 0.125% test formulation group.

Significant decrease of 19% and 14%, in serum phospholipids was also seen in the animals fed the formulation of 0.5 and 1.0% level, respectively.

Liver total lipids were significantly higher in diet groups with 0.125% and 0.25% test formulation: there was a concomitant higher accumulation of triglycerides in the liver in these two diet groups.

Thus, the test formulation has produced the hypotriglyceridimic effect at all the levels tested. The dose effect is also seen as shown in Table 3, below, and FIG. 3.

TABLE 1

Fasting serum triglyceride levels in patients before and after treatment

|  | TG1 | TG2 | TG3 | DELTA = (TG1 − TG3) | (DELTA/TG1) ×100 |
|---|---|---|---|---|---|
| 1 | 430 | 360 | 180 | 250 | 58.14 |
| 2 | 336 | 252 | 178 | 158 | 47.02 |
| 3 | 504 | 364 | 280 | 224 | 44.44 |
| 4 | 583 | 400 | 340 | 243 | 41.68 |
| 5 | 379 | 212 | 180 | 199 | 52.15 |
| 6 | 404 | 240 | 186 | 218 | 53.96 |
| 7 | 284 | 196 | 164 | 120 | 42.25 |
| 8 | 548 | 415 | 380 | 168 | 30.65 |
| 9 | 476 | 299 | 240 | 236 | 49.58 |
| 10 | 308 | 322 | 175 | 133 | 43.18 |
| Mean | 425.2 | 306.0** | 230.3** | 194.9 | 46.34 |
| SD | 101.65 | 78.54 | 77.62 | 47.1 | 7.78 |

TG1 (mg/dl): Before treatment
TG2 (mg/dl): 3 weeks after treatment
TG3 (mg/dl): 6 weeks after treatment
**$p < 0.0005$ as compared to TG1

TABLE 3

Serum triglycerides in test formulation fed hyperlipidemic rats

| DIET GROUP | TOTAL | LDL-VLDL | HDL |
|---|---|---|---|
| Hyperlipidemic: CONTROL | 320.6 ± 20.5 | 172.3 ± 12.5 | 148.3 ± 7.0 |
| 0.125% FORMULATION | 197.6 ± 9.74* | 128.3 ± 4.1* | 69.3 ± 7.0* |
| 0.25% FORMULATION | 221.4 ± 16.5* | 147.1 ± 6.5 | 74.3 ± 10.4 |
| 0.5% FORMULATION | 156.8 ± 10.4* | 127.0 ± 4.3* | 29.8 ± 6.5* |
| 1.0% FORMULATION | 146.5 ± 9.33* | 104.8 ± 4.9* | 41.7 ± 5.5* |

TABLE 3-continued

Serum triglycerides in test formulation fed hyperlipidemic rats

| DIET GROUP | TOTAL | LDL-VLDL | HDL |
|---|---|---|---|
| 5.0% FORMULATION | 180.4 ± 3.69* | 141.8 ± 10.3 | 38.6 ± 4.8* |
| NORMAL CONTROL | 137.5 ± 3.33 | 84.0 ± 6.8 | 53.5 ± 2.2 |

*significant decrease compared to control group

It is to be understood that the present invention is not limited to the sole embodiments described above, but encompasses any and all embodiments within the scope of the following claims.

I claim:

1. A composition for the reduction of triglycerides and total cholesterol in a hyperlipidemic patient, comprising:
    an effective amount of vanillin for reducing triglycerides and total cholesterol;
    an effective amount of ascorbic acid for protecting an aldehyde group in the vanillin; and
    an effective amount of ethylenediaminetetraacetic acid for preserving the ascorbic acid in a reduced state.

2. The composition according to claim 1, consisting of 20 to 2,000 milligrams of the vanillin.

3. The composition according to claim 1, consisting of 10 to 15 milligrams of the ascorbic acid.

4. The composition according to claim 1, consisting of 5 to 10 milligrams of the ethylenediaminetetraacetic acid.

5. The composition according to claim 1, formulated into a dosage form selected from the group consisting of a capsule, a tablet, a pill and a powder.

6. The composition according to claim 1, wherein the composition is combined with a fatty food as a food additive.

7. The composition according to claim 1, wherein the composition is admixed in a beverage as a food additive.

8. A method for the prevention and reduction hypertriglyceridemia and the reduction of total cholesterol in a patient, comprising administering to the patient a therapeutically effective amount of the composition according to claim 1.

9. The method according to claim 8, wherein the composition is combined with a fatty food as a food additive for administering to the patient.

10. The method according to claim 8, wherein the composition is admixed in a beverage as a food additive for administering to the patient.

11. A gelatin capsule for the reduction of triglycerides and total cholesterol in a hyperlipidemic patient, comprising:
    20 to 2,000 milligrams of vanillin;
    10 to 15 milligrams of ascorbic acid; and
    5 to 10 milligrams of ethylenediaminetetraacetic acid.

12. Method of reducing triglycerides and total cholesterol in a hyperlipidemic patient, comprising administering a daily dosage of the gelatin capsule according to claim 11 to the patient.

* * * * *